United States Patent
Nelson et al.

(10) Patent No.: US 9,050,117 B2
(45) Date of Patent: Jun. 9, 2015

(54) DYNAMIC COOLING OF HUMAN SKIN USING A NONTOXIC CRYOGEN WITH NO OZONE DEPLETION AND MINIMAL GLOBAL WARMING POTENTIAL

(75) Inventors: J. Stuart Nelson, Laguna Niguel, CA (US); Lars O. Svaasand, Trondheim (NO)

(73) Assignee: The Regents of the University of California, Oakland, CA (US)

(*) Notice: Subject to any disclaimer, the term of this patent is extended or adjusted under 35 U.S.C. 154(b) by 1894 days.

(21) Appl. No.: 11/845,503

(22) Filed: Aug. 27, 2007

(65) Prior Publication Data

US 2008/0071332 A1    Mar. 20, 2008

Related U.S. Application Data (60) Provisional application No. 60/840,867, filed on Aug. 28, 2006.

(51) Int. Cl.
```
A61F 2/00      (2006.01)
A61B 18/20     (2006.01)
C09K 5/06      (2006.01)
A61B 18/02     (2006.01)
A61B 18/00     (2006.01)
```

(52) U.S. Cl.
CPC ............... *A61B 18/203* (2013.01); *A61B 18/02* (2013.01); *A61B 18/20* (2013.01); *A61B 2018/00029* (2013.01); *A61B 2018/00452* (2013.01); *C09K 5/06* (2013.01)

(58) Field of Classification Search
CPC ...... A61B 18/02; A61B 18/20; A61B 18/203; A61B 2018/00452; A61F 2007/0059; A61F 2007/006; A61F 2007/0063; A61F 2007/0064; A61F 2007/0065; A61F 2007/0066; A61F 2007/0067; A61F 2007/0068; C09K 5/06; A61N 5/06
USPC ................. 607/100, 107, 99, 108, 89, 94, 96; 606/2, 3, 9–12, 20–26; 128/898; 252/67; 62/384, 50.2
See application file for complete search history.

(56) References Cited

U.S. PATENT DOCUMENTS

| | | | |
|---|---|---|---|
| 4,495,993 A | 1/1985 | Andersen | |
| 5,814,040 A * | 9/1998 | Nelson et al. | 606/9 |
| 6,141,985 A * | 11/2000 | Cluzeau et al. | 62/293 |
| 6,514,244 B2 * | 2/2003 | Pope et al. | 606/9 |
| 2002/0042609 A1 | 4/2002 | Kelman et al. | |

(Continued)

OTHER PUBLICATIONS

Di Nicola et al. "Blends of carbon dioxide and HFCs as working fluids for the low-temperature circuit in cascade refrigerating systems," Int'l J of Refrigeration, vol. 28, pp. 130-140, 2005.*

(Continued)

*Primary Examiner* — Cris L Rodriguez
*Assistant Examiner* — Mirayda A Aponte
(74) *Attorney, Agent, or Firm* — Marcus C. Dawes; Daniel L. Dawes (57) ABSTRACT

An improvement in a method for providing localized cooling of tissue when thermally mediated by electromagnetic radiation including directing at least one spurt of a heat transferring substance onto a selected location on the tissue, and preventing ignition of the heat transferring substance by heating from the electromagnetic radiation. Preferably liquid carbon dioxide under pressure is supplied as the heat transferring substance, and adiabatically expanded to provide a solid carbon dioxide spray onto the selected location.

5 Claims, 5 Drawing Sheets

(56) References Cited

U.S. PATENT DOCUMENTS

| | | |
|---|---|---|
| 2002/0120258 A1 | 8/2002 | Lalonde |
| 2002/0183811 A1* | 12/2002 | Irwin .............................. 607/94 |
| 2003/0036749 A1* | 2/2003 | Durkin et al. ..................... 606/3 |
| 2004/0167505 A1 | 8/2004 | Joye et al. |
| 2005/0253107 A1 | 11/2005 | Flynn et al. |
| 2006/0030843 A1 | 2/2006 | Lane et al. |

OTHER PUBLICATIONS

International Searching Authority, The International Search Report and the Written Opinion for PCT/US07/76913 dated Jan. 31, 2008, 9 pages.

* cited by examiner

DYNAMIC COOLING OF HUMAN SKIN USING A NONTOXIC CRYOGEN WITH NO OZONE DEPLETION AND MINIMAL GLOBAL WARMING POTENTIAL

The present application is related to U.S. Provisional Patent Application Ser. No. 60/840,867, filed on Aug. 28, 2006, which is incorporated herein by reference and to which priority is claimed pursuant to 35 USC 119.

This invention was made with Government support under grants AR047551 and GM062177 awarded by the National Institute of Health. The Government has certain rights in the invention.

BACKGROUND OF THE INVENTION

1. Field of the Invention

The invention relates to the field of therapeutic treatment of skin or tissue by exposure to light or other electromagnetic radiation in combination with cryogen cooling of the irradiated tissue.

2. Description of the Prior Art

An important issue in laser treatment of cutaneous lesions is to protect the epidermis from thermal damage. This heating, which is primarily caused by light absorption in the melanosomes, can easily bring the temperature of the basal layer above the threshold damage value of 65-70° C. Precooling of the epidermal basal layer from the normal value of 35° C. to 0° C. increases the optical radiant exposure that can be safely delivered by a factor of two.

Selective epidermal cooling can be obtained by exposing the skin surface to a cryogen for an interval of time corresponding to the thermal diffusion time from the stratum corneum through the epidermis and down to the basal layer. Thus, the upper layers are cooled while leaving the temperature of dermal and subcutaneous layers unchanged. Currently, selective epidermal cooling is achieved using a liquid spray of the cryogen R-134a (tetrafluoroethane) for 30-100 ms immediately before laser exposure. A typical procedure is to spray the surface for 30-50 ms, and then expose the skin to laser irradiation 20-30 ms after the end of the cryogen spurt.

Tetrafluoroethane ($H_2FC\text{—}CF_3$) is a chlorine free hydrofluorocarbon (HFC), thus representing no damage to the ozone layer. However, recent studies suggested that the non-$CO_2$ greenhouse gases such as methane ($CH_4$), nitrous oxide ($N_2O$), hydrofluorocarbon (HFC), perfluorocarbon (PFC) and sulphur hexafluoride ($SF_6$) can make a significant contribution to global warming in comparatively low concentrations.

Table 1 gives the global warming potential (GWP) for frequently used gases. (The GWP of $CO_2$ is defined as unity)

TABLE 1

Major GWP Gases in the United States (100-year global warming potentials)[a]

| Gas | GWP | Atmospheric Lifetime | Source of Emissions |
|---|---|---|---|
| HFC-23 | 11,700 | 264 | HCFC-22 Production, Fire Extinguishing Equipment, Aerosols, Semiconductor Manufacture |
| HFC-43-10mee | 1,300 | 17.1 | Solvents |
| HFC-125 | 2,800 | 32.6 | Refrigeration/Air Conditioning |
| HFC-134a | 1,300 | 14.6 | Refrigeration/Air Conditioning, Aerosols, Foams |
| HFC-143a | 3,800 | 48.3 | Refrigeration/Air Conditioning |
| HFC-152a | 140 | 1.5 | Refrigeration/Air Conditioning, Aerosols, Foams |
| HFC-227ea | 2,900 | 36.5 | Aerosols, Fire Extinguishing Equipment |
| HFC-236fa | 6,300 | 209 | Refrigeration/Air Conditioning, Fire Extinguishing |
| SF6 | 23,900 | 3,200 | Electricity Transmission/ Distribution; Magnesium Production; Semiconductor Manufacturing |
| PFCs (primarily CF4, C2F6) | 6,500-9,200 | 10,000-50,000 | Aluminum Smelting, Semiconductor Manufacture, Fire Extinguishing |
| PFC/PFPEsb | 7,400 | 3,200 | Solvents |

[a]Note that this table lists major commercial gases and sources; other minor gases and uses such as lab applications are not listed here. The GWPs and atmospheric lifetimes are taken from Climate Change 1995, the IPCC Second Assessment Report.
[b]PFC/PFPEs are a diverse collection of PFCs and perfluoropolyethers (PFPEs) used as solvents.

Tetrafluoroethane R-134a, which is non-toxic, non-flammable, and non-ozone depleting, has a boiling point (b.p.) of −26° C. at 1 atm. These properties make it an excellent choice for cryogen spray cooling of human skin. However, R-134a has a comparatively high GWP of 1,300. Therefore, substitutes for R-134a for use in large scale applications such as air conditioners for cars, home appliances and manufacturing of thermally insulating polystyrene foams are being developed. As a result, carbon dioxide based air conditioners are being introduced for the car industry and non-fluorinated, but flammable, gases are used in home appliances today. The lowest GPW value (GWP=140) in table 1 is that of R152a (difluoroethane, $F_2HC\text{—}CH_3$), but this compound autoignites at 455° C.

The GWP values for non-fluorinated hydrocarbons such as propane ($C_3H_8$, R-290, b.p. −42.1° C.), butane ($C_4H_{10}$, R-600, b.p −0.5° C.) and isobutene (R-600a, b.p −12° C.) are very low because they are rapidly broken down in the atmosphere. The global warming potential of propane is GWP=3 and that of butane is less than 10.

Potential non-flammable candidates for cryogen spray cooling could be carbon dioxide ($CO_2$, R-744) or nitrous oxide ($N_2O$, R-744a) but, unfortunately, these compounds do not form boiling liquids at atmospheric pressure. Liquid $CO_2$ results in dry-ice formation immediately after leaving the outlet nozzle. The skin surface will therefore be covered with a layer of dry-ice crystals. Possible reduction in the heat transfer coefficient due to build up of a porous layer of dry ice crystals can be avoided by having an adequate high momentum flux of the spray.

Liquid nitrogen ($N_2$, b.p. −90° C.) is an environmentally safe, non-toxic and liquid forming cryogen which has been extensively used in dermatology. However, the evaporation loss is high, and the cryogenic equipment for delivering liquid cryogen spurts in the 100 ms range might be technically very cumbersome.

Interesting candidates are also in the group of flammable hydrocarbons, which are used today in medical applications. The commercial product Histofreezer®, which is used for the treatment of cervical bleeding and removal of warts, is composed of a mixture of dimethyl ether ($C_2H_6O$, b.p. −22° C.), propane and isobutene. Further on, these compounds are also used as propellants for hair lacquers, etc.

The use of a flammable cryogen during laser exposure for, e.g., hair removal requires special precautions. The pulse energy, which typically can be in the range of 20-70 $J/cm^2$, can ignite the hair above the skin surface. Thus, the combined use of flammable cryogen and high laser energy might induce burns to the skin.

The dynamic cooling principle as defined in U.S. Pat. No. 5,814,040, which is incorporated herein by reference, represents a simple, reliable and efficient method for protection of the epidermis, and for some applications such as pulsed laser treatment of port wine stain lesions it represents the only choice for efficient protection. Port wine stain is a congenital lesion with a frequency of one in two hundred births, often resulting in a high psychological burden for the child.

What is needed is to find an efficient substitute for tetrafluoroethane that is compatible with requirements for low global warming potential.

BRIEF SUMMARY OF THE INVENTION

The illustrated embodiment of the invention is an improvement in a method for providing localized cooling of tissue or skin when thermally mediated by electromagnetic radiation or a laser comprising the steps of directing at least one spurt of or applying a predetermined amount of a flammable heat transferring substance onto a selected location on the tissue and preventing ignition of the heat transferring substance by heating from the electromagnetic radiation.

In one embodiment the step of directing at least one spurt of a heat transferring substance onto a selected location on the tissue comprises directing a potentially flammable coolant onto the selected location and where preventing ignition of the heat transferring substance by heating from the electromagnetic radiation comprises isolating or shielding the heat transferring substance from oxygen in an ambient environment.

In another embodiment the step of preventing ignition of the heat transferring substance by heating from the electromagnetic radiation comprises mixing a potentially flammable coolant with an inert substance to provide a substantially nonflammable mixture prior to directing at least one spurt of the heat transferring substance mixed with the inert substance onto a selected location on the tissue.

In still another embodiment the step of preventing ignition of the heat transferring substance by heating from the electromagnetic radiation comprises employing an inert heat transfer substance as the heat transferring substance.

The step of employing an inert heat transfer substance comprises employing liquid carbon dioxide under pressure as the heat transferring substance, and adiabatically expanding the liquid carbon dioxide to provide a solid carbon dioxide spray onto the selected location.

In still a further embodiment the step of preventing ignition of the heat transferring substance by heating from the electromagnetic radiation comprises employing a substantially nonflammable liquid propane and/or butane mixed with liquid carbon dioxide under pressure as the heat transferring substance, and adiabatically expanding the liquid propane or butane mixture with liquid carbon dioxide to provide a slurry or mixture of liquid propane or butane with solid carbon dioxide onto the selected location.

The illustrated embodiment also includes an apparatus for performing any one of the foregoing improvements in a method.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

The principles presented below provide a solution to the problem of finding an efficient substitute for tetrafluoroethane that is compatible with requirements for low global warming potential. In order to prevent cryogen ignition during pulsed laser exposure, one or more of the following methods are used.

Shielding Gas

The method of using a shielding gas to prevent oxygen from arriving at the heated spot is well established in electrical welding. Oxygen from the surrounding air is prevented from oxidizing the welding spot by using a shield of inert gas. A circular orifice mounted concentrically with the electrode can deliver the shielding gas. Examples of this technique are MIG (metal-inert-gas) welding where an inert gas surrounds the electrode, or TIG (tungsten-inert-gas) welding where a tungsten electrode heats up the welding materials. Typical shielding gases are inert gases such as argon, but nitrogen and carbon dioxide can also be used. This principle could be used to prevent ignition of flammable cryogens during dynamic cooling such a diagrammatically depicted in FIG. 1. Liquid cryogen from a source 10 is supplied under pressure to a central tube 16 while a shielding gas from a source 12 is supplied to a concentric tube 14. The liquid cryogen exits from a nozzle or orifice 22 which is located downstream from a concentric outer nozzle or orifice 20 through which the shielding gas exits. What results is a shielded spray 16 which impinges on skin or tissue 18 in which the contingently inflammable cryogen is surrounding by a shielding cone of noncombustible gas. Laser light or another energy source which is then directed to the same impingement point on skin 18 thus does not ignite the cryogen even though ignition temperatures might be temporarily reached, because the cryogen is shielded from access to oxygen in the ambient.

Figure 1:
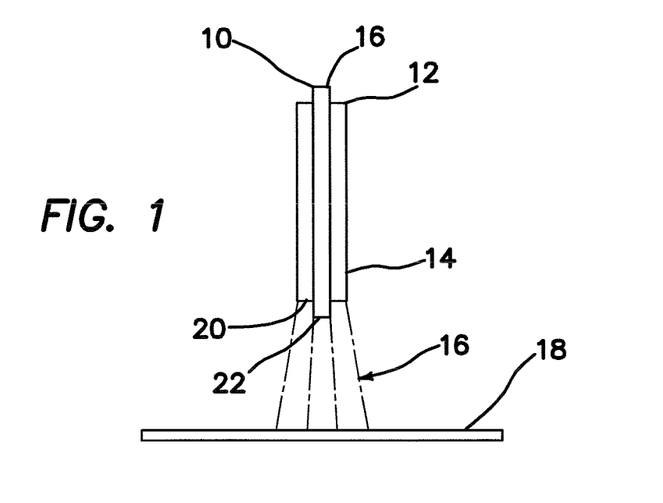
FIG. 1 is a diagram illustrating a method of liquid cryogen cooling using an inert shielding gas.

The arrangement shown in FIG. 1 enables the use of flammable cryogens such as dimethyl ester, propane, isobutene or any mixture of these compounds. The inert shielding gas can be argon or carbon dioxide gas. Two separate gas valves, one for the liquid cryogen and a second one for the shielding gas must be used. In principle, the shielding gas valve should be opened before the cryogen valve and left open until after the laser energy has been delivered. The flammability ranges of hydrocarbons in air are quite narrow as the range limits for ignition is 2.2 to 9.6% in a propane/air mixture, 1.5 to 8.5% for butane/air mixture and 3.4 to 17% for dimethyl ether/air mixture. The flame extinguishing concentrations for n-heptane ($C_7H_{16}$) flames in air have been reported to 33.6, 43.3 and 22% for, respectively, $N_2$, Ar and $CO_2$. The required amount of shielding gas for flame-extinguishing or ignition-preventing properties is dependent on the details in the mixing process of hydrocarbon, shielding gas and air.

Mixture of Liquid Flammable Cryogen with Shielding Gas

Figure 2:
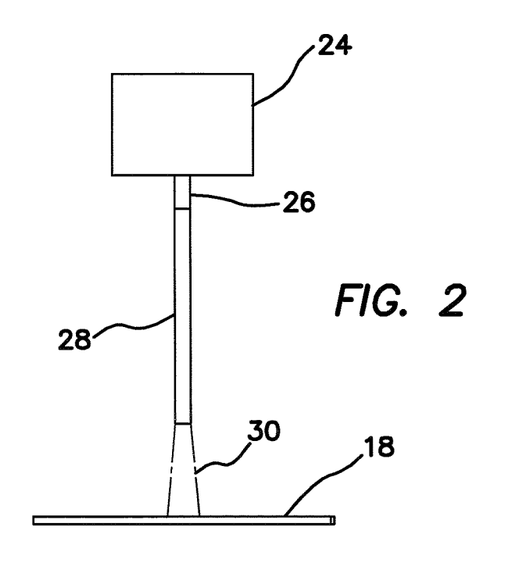
FIG. 2 is a diagram illustrating a method of using a mixture of liquid flammable cryogens and carbon dioxide supplied from a pressurized container.

Another embodiment of the method is based on mixing a flammable cryogen with an inert gas before application of the mixture. The technique of mixing nonflammable propellants with flammable ones is frequently used, e.g. R-134a is mixed with a flammable propellant such as propane and butane to prevent ignition. In the present case, carbon dioxide can be mixed with liquid cryogen in the same pressurized container and sprayed onto the skin surface through the same valve and nozzle as depicted in the diagram of FIG. 2. The premixed gases are contained with a pressurized container 24 and controlled by a valve 26 to a nozzle 28 from which exits a spray 30 of the gas mixture impinging on skin 18.

Adiabatic expansion of liquid carbon dioxide when leaving the nozzle 28 will not cool the constituents of the flammable mixture below their respective freezing points, since the freezing points for propane, butane, isobutane and dimethyl ether are −190, −138, −159 and −142° C., respectively. The properties of a mixture of propane and carbon dioxide are also strongly dependent on the mixing ratios. A pressurized mixture of, e.g., 50% liquid propane and 50% liquid carbon dioxide at room temperature has a pressure of 3.7 MPa, i.e., which is 35% lower than for 100% $CO_2$. Further, propane at less then 9.4% in carbon dioxide is by federal regulation classified as a non-flammable mixture.

Liquid Carbon Dioxide Cooling.

The use of flammable cryogens with shielding gas requires separate FDA approval for use in medical treatments. Therefore, it would be advantageous if all flammable compounds could be avoided. A potential candidate, which would satisfy the requirements for low global warming potential and is completely non-flammable, is carbon dioxide, i.e., R744. Carbon dioxide is toxic in high concentrations, i.e. above 10% in air and might be lethal in concentrations above 20%, but it is completely safe and harmless in low concentrations, e.g., exhaled air contain up to 4%.

Figure 3:
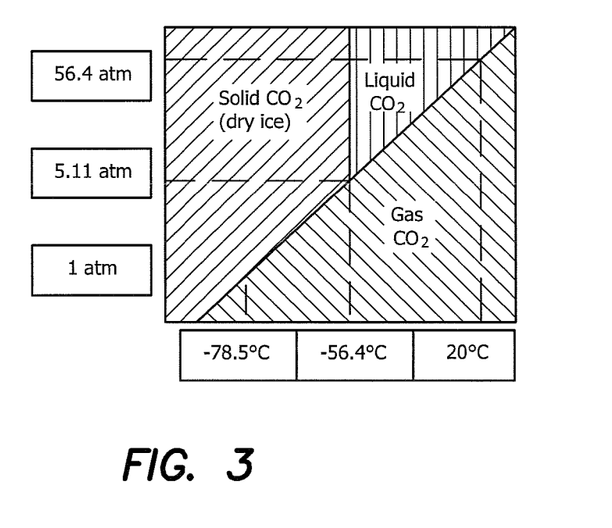
FIG. 3 is a phase diagram of carbon dioxide.

Carbon dioxide has a triple point where liquid, solid and gas coexist at −56.4° C. at 5.11 atm. pressure as graphically depicted in the phase diagram of FIG. 3. Below this pressure only the solid and gas phase coexist, and solid carbon dioxide, i.e. dry ice, will sublimate directly into gas. The gas pressure for the liquid at room temperature is 5.72 MPa (56.4 atm.). When liquid $CO_2$ is released into air at atmospheric pressures it evaporates adiabatically forming dry ice at −78.5° C. with a latent heat of sublimation of 571.3 kJ/kg.

Figure 4:
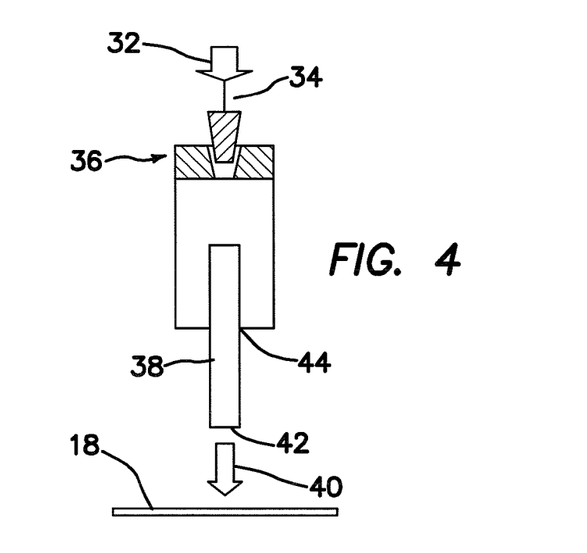
FIG. 4 is a diagram illustrating an apparatus for providing carbon dioxide supplied from a pressurized container as a solid cryogen sprayed onto the skin.

In an experimental setup as diagrammatically illustrated in FIG. 4, a high-pressure steel container with 5 kg liquid CO.sub.2 was connected to a valve via a 1 m long high pressure flexible tube 34 connected to a valve 36, which in the illustrated embodiment was a Parker Hannifin Corp. Fairfield N.J. series 99, with a controlled release of a liquid carbon dioxide pulse at a pressure of up to 8.62 MPa (85.1 atm.), 0.8 mm orifice. In order to fill the entire connecting system with liquid carbon dioxide, the steel container 32 was mounted upside down and the valve 36 was thoroughly purged. The valve 36 could be equipped with several different nozzles made by cylindrical steel tubes 38 having a distal outlet nozzle 42. The bore of the tubes 38 were 0.25, 0.5 and 0.7 mm in diameter and the length was 20 mm. Additionally, experiments were done without tubes 38. In that case, the outlet nozzle 44 comprised a mounting nut with 1.6 mm diameter bore and about 5 mm length. The length of spray 40 or the distance from the nozzle opening 42 or 44 to the object or skin 18 being cooled was variously set at 30 or 50 mm. The temperature distribution of a sprayed object was measured with a film-microthermocouple mounted on a 10 mm thick epoxy slab. The thermal properties of epoxy are close to those of skin, thus the epoxy slab served as a tissue phantom.

Figure 5:
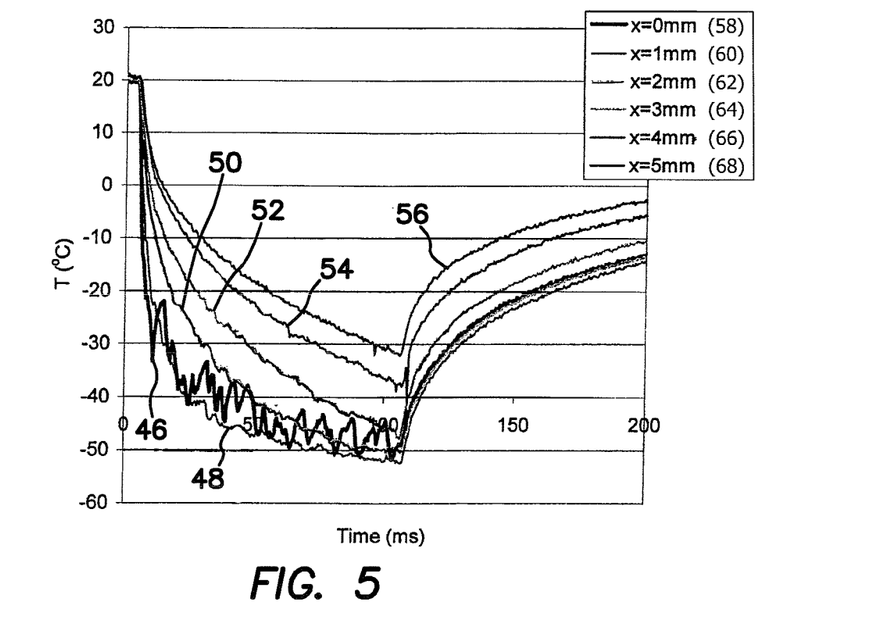
FIG. 5 is a graph of temperature of a target surface as a function of distance from the center of the impingement as measured in the apparatus of FIG. 4 for a spray duration of 100 ms provided by a nozzle bore 0.7 mm at a 30 mm distance from the target surface.

The results from spaying with the 0.7 mm diameter bore nozzle at 30 mm distance is shown in the graph of FIG. 5. The graph shows the temperature distribution during and after a 100 ms long spurt at five different distances from the center of the spray, namely curves 46-56 correspond to distances from the center of 0-5 mm in 1 mm increments respectively. The temperature at the center exhibits somewhat erratic temperature fluctuations, which is believed due a tendency to build up dry ice in that region. At 1 mm from the center the temperature fluctuations are significantly reduced. The temperature at 1 mm from the center drops down to −47° C. after 50 ms and further down to −52° C. at 100 ms. The corresponding values at 5 mm from the center are −20° C. and −31° C. at 50 and 100 ms respectively.

Figure 6:
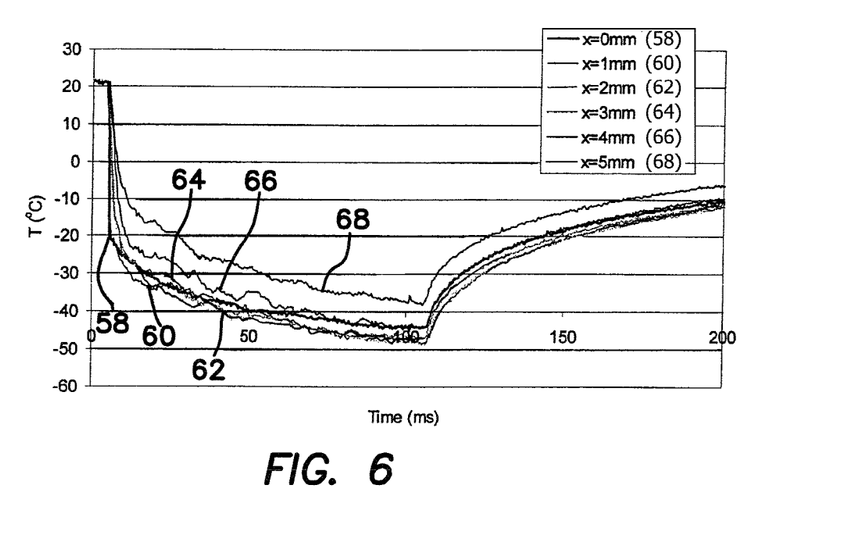
FIG. 6 is a graph of temperature of a target surface as a function of distance from the center of the impingement as measured in the apparatus of FIG. 4 for a spray duration of 100 ms provided by a larger nozzle bore of 1.6 mm at a 30 mm distance from the target surface.

The corresponding results for the 1.6 mm bore nozzle 38 are given in the graph of FIG. 6. This nozzle 38 gives better uniformity. As in the case with the graph of FIG. 5, FIG. 6 shows the temperature distribution during and after a 100 ms long spurt at five different distances from the center of the spray, namely curves 58-68 correspond to distances from the center of 0-5 mm in 1 mm increments respectively. The temperature drop at 1 mm from the center after 50 ms and 100 ms are, −40° C. and −48° C. The corresponding values at 5 mm from the center are −30° C. and −38° C. respectively.

The cooling efficiency of the 0.5 mm bore nozzle 38 was somewhat less than for the 0.7 mm, but still had acceptable performance. However, the 0.25 mm nozzle exhibited poor performance. This nozzle 38 produced very little dry ice and the surface was primarily hit by cold $CO_2$ gas.

The efficiency of the nozzles 38 at a distance of 50 mm was also investigated. However, neither the lateral coverage of the spray 40 nor the temperature drop was improved. If a wider area than about 10 mm diameter needs to be cooled, application of multiple simultaneously spraying nozzles 38 could be employed.

Figure 7:
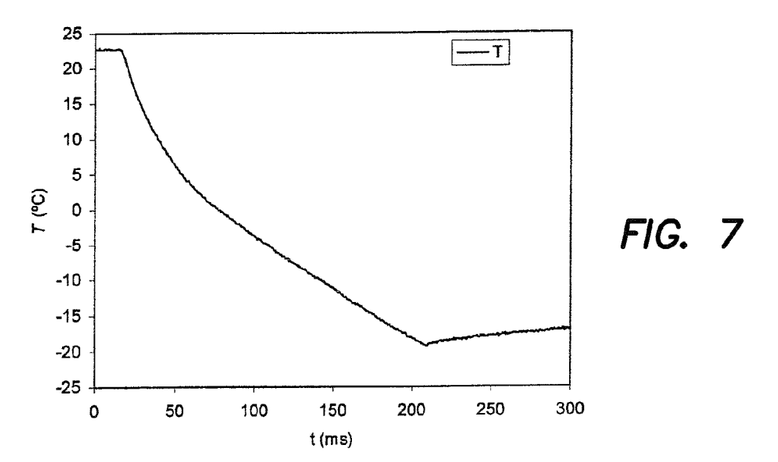
FIG. 7 is a graph of disk temperature versus spray time for a nozzle bore 0.7 mm, 30 mm distance in a heat transfer measurement device.

The heat transfer was measured by spraying a cylindrical silver disk embedded in the surface of an epoxy slab as described in U.S. Pat. No. 6,669,688, which is incorporated herein by reference. The diameter and height of the disk were, respectively, 7.2 mm and 0.42 mm. The specific weight of silver is 10,500 $kg/m^3$ and the specific heat is 232 J/kgK. Thus, the heat capacity of the disk is 0.042 J/K. The temperature drop versus spraying time for the 0.7 mm bore nozzle 38 at 30 mm distance is given in the graph of FIG. 7. Spay was directed normal to the disk and centered at the disk. The heat transfer coefficient H between the dry ice at −78.5° C. and the silver disk at initially 23° C. can be determined from the thermal relaxation time τ of the silver disk using $$H = \frac{\rho C d}{\tau} \quad (1)$$

where ρ, C and d are, respectively, the specific weight, specific heat and the thickness of the disk. The results of FIG. 7 are summarized in table 2.

TABLE 2

| | Spray duration | | | |
|---|---|---|---|---|
| | 50 ms | 100 ms | 150 ms | 200 ms |
| Heat transfer coefficient | 4500 $W/m^2K$ | 3600 $W/m^2K$ | 3100 $W/m^2K$ | 3700 $W/m^2K$ |
| Total heat extraction | 0.8 J | 1.2 J | 1.5 J | 1.8 J |
| Average heat extraction | 2.0 $J/cm^2$ | 3.1 $J/cm^2$ | 3.8 $J/cm^2$ | 4.4 $J/cm^2$ |
| Required dry ice consumption. | 1.4 mg | 2.1 mg | 2.6 mg | 3.1 mg |

The heat transfer coefficient for tetrafluoroethane, R134a, sprayed onto a 10 mm diameter, 1 mm thick silver disk with a 0.7 mm bore nozzle at 50 mm distance has been reported to H=7500 $W/m^2K$ for a spurt duration of 100 ms. The measured heat transfer coefficient for carbon dioxide was about 50% less than this value. One contributing factor to this reduction might be the nonuniformity of the temperature distribution for the 0.7 mm bore nozzle 38, where the temperature drops for 50-100 ms spurts were about 30% less at 4-5 mm distance as compared to the center as shown in the graph of FIG. 5. The heat extraction for the 1.6 mm bore nozzle 38, which had more uniform temperature distribution, was somewhat higher than for the 0.7 mm nozzle 38, e.g., the heat extraction after a 50 ms spray with the first nozzle 38 was about 15% higher than for the latter one. However, the much lower sublimation point of dry ice of −78.5° C. might partly compensate for the reduction in heat coefficient as compared to tetrafluoroethane since the boiling point of the latter is −26.5° C. at 1 atm.

The measured heat extraction is, however, quite adequate for cooling the 60-100 μm thick epidermis of normal human skin from ambient skin temperature of 35° C. to 0° C. This corresponds to a heat extraction in the range of 0.9-1.5 $J/cm^2$, which according to the results given in Table 2 can be obtained by spurts in the range of 25-45 ms duration.

The liquid carbon dioxide consumption and the amount of dry ice in the spray was evaluated by collecting the mixture of gas/dry ice in a closed plastic bag. The volume of the content increased more then 10 times when all dry ice had sublimated after about 30 s as compared to the volume immediately after the spurt. Thus, the cryogen spray contained more than 90% of dry ice by weight. The consumption for the various nozzles 38 for a 100 ms spurt are summarized in Table 3.

TABLE 3

| | Nozzle bore | | | |
|---|---|---|---|---|
| | 1.6 mm | 0.7 mm | 0.5 mm | 0.25 mm |
| $CO_2$ | 0.7 g | 0.7 g | 0.45 g | 0.15 g |

The carbon dioxide consumption for the 1.6 mm and the 0.7 mm nozzles 38 were about the same. The reason was that maximum output was limited by the 0.8 mm diameter orifice of the valve 36 itself as depicted in FIG. 4. The required dry ice formation for cooling a tissue surface 18 is a very small fraction of the liquid cryogen consumption, e.g. the required amount of dry ice for cooling a 100 μm thick epidermal layer of 5 mm radius from 37° C. to 0° C. is about 2 mg. Thus, the $CO_2$ consumption could in principle be reduced by proper optimization of the nozzle 38. However, the present consumption might be quite acceptable, e.g. spraying with the 1.6 mm or the 0.7 mm bore for 50 ms corresponds to a cooling capacity of about 3000 spurts per kg carbon dioxide.

Figure 8A:
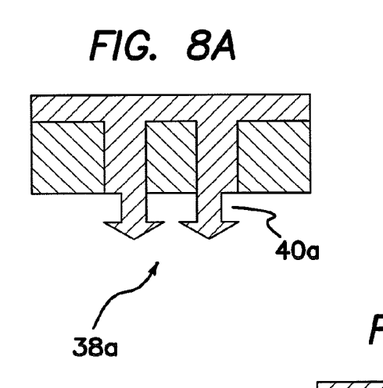
FIG. 8a is a simplified side cross sectional view of an alternative embodiment comprising a plurality of nozzles provided in a parallel array with a corresponding pattern of parallel sprays.
Figure 8B:
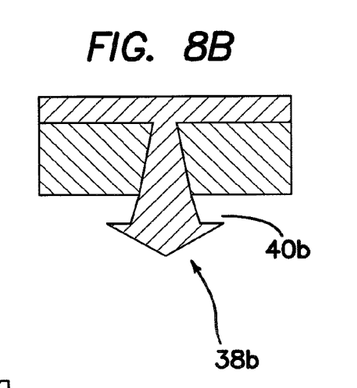
FIG. 8b is a simplified side cross sectional view of an alternative embodiment where the nozzle is provided in the shape of an inverted cone to provide a diverging spray.
Figure 8C:
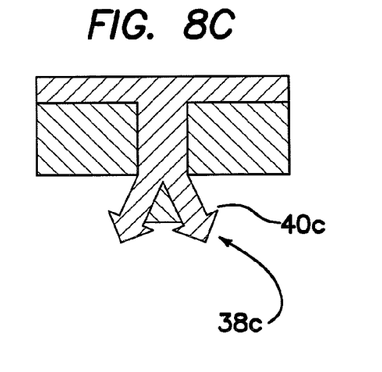
FIG. 8c is a simplified side cross sectional view of an alternative embodiment where the nozzle is provided with a plurality of orifices communicated to the same tube to provide a patterned spray.

In the case of laser irradiation of larger spots, e.g. 18 mm diameter, multiple nozzles or specifically designed nozzles might be necessary. FIGS. 8a-8c show sketches of various nozzles design for improving the uniformity of the spray over large spot sizes. FIG. 8a is an embodiment where a plurality of nozzles 38a are provided in a parallel array with a corresponding pattern of parallel sprays 40a. FIG. 8b is an embodiment where nozzle 38b is diverging or provided in the shape of an inverted cone to provide a diverging spray 40b. FIG. 8c is an embodiment where nozzle 38c is provided with a plurality of orifices communicated to the same tube to provide a patterned spray 40c as determined by the pattern and angulation of the bores defined in the nozzle 38c like a showerhead. Similarly, nozzle 38 may be provided with an adjustable spray head so that the user may change the spray pattern from one use to another. It is to be understood that these embodiments do not exhaust the possibilities for nozzle arrays or designs, all of which are expressly contemplated as being within the scope of the invention.

Consider also the acoustical noise generated by the adiabatic expansion of carbon dioxide. This noise level, which can be disturbing to a patient, can be reduced by a conventional silencer. Similarly, the force of the spray 40 onto the skin surface 18 can be varied not only by means of the delivery pressures, but by use of various types of conventional gas diffusers combined with nozzle 38.

Liquid Propane Cooling.

Figure 9A:
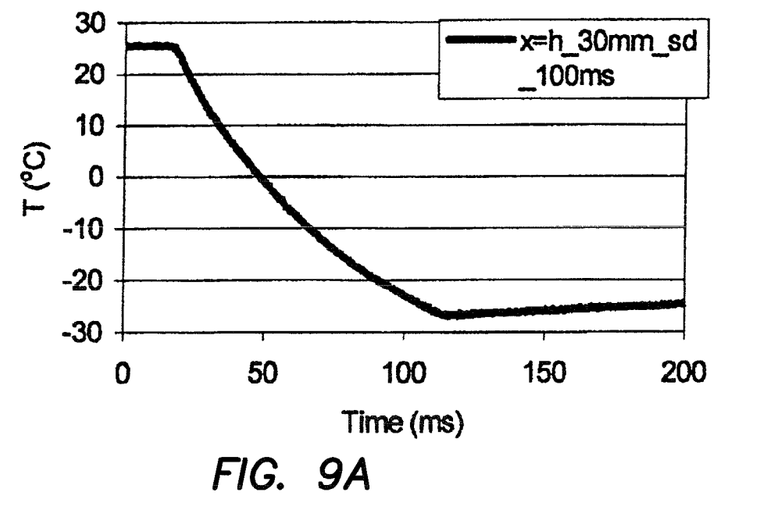
FIG. 9a is a graph of the disk temperature versus spray time for propane using a nozzle bore 0.7 mm at 30 mm distance.
Figure 9B:
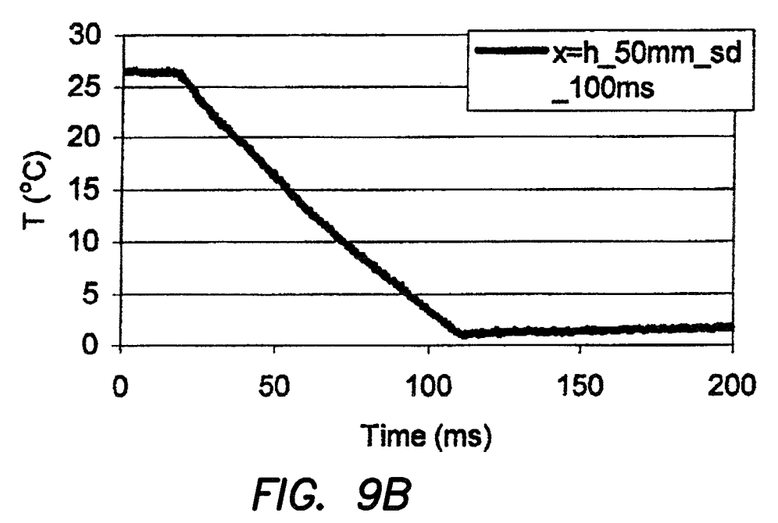
FIG. 9b is a graph of the disk temperature versus spray time for propane using a nozzle bore 0.7 at 50 mm distance.

The cooling efficiency with propane was investigated with the same silver disk detector as discussed above for carbon dioxide measurements. The propane was of commercial quality for soldering/heating application marketed in a pressurized canister containing 0.4 kg liquid propane as sold by Bernzomatic, of Medina N.J. Typical results are shown in the graphs of FIGS. 9a and 9b. The results are summarized in table 4.

TABLE 4

| | Spray duration/distance | | | |
|---|---|---|---|---|
| | 50 ms/30 mm | 100 ms/30 mm | 50 ms/50 mm | 50 ms/50 mm |
| Heat transfer coefficient | 15 000 W/m$^2$K | 17 000 W/m$^2$K | 3900 W/m$^2$K | 4500 W/m$^2$K |
| Total heat extraction | 1.5 J | 2.3 J | 0.5 J | 1.0 J |
| Average heat extraction | 3.8 J/cm$^2$ | 5.7 J/cm$^2$ | 1.2 J/cm$^2$ | 2.5 J/cm$^2$ |

The heat transfer coefficient for a 50 ms long propane spurt at 30 mm distance was about twice as large as reported for tetrafluoroethane under the similar conditions. One reason for the high heat transfer coefficient could be that the propane spray adhered very well to the surface 18. It is not clear whether this phenomenon was due to propane itself or to the sulphuric odor compound added to propane by the manufacturer for leak detection. The efficacy dropped off rapidly with distance, and the coefficient dropped down by about 75% at 50 mm distance, i.e., to about the same value as for carbon dioxide at 30 mm distance. (See Table 2).

The gas consumption was very low. A 100 ms long spurt of propane delivered by the 0.7 mm bore nozzle 38 was 80 ml gas at atmospheric pressure, which corresponds to 0.14 g liquid propane. Propane has, as discussed before, a range of flammability of 2.2-9.6% by volume in air. Thus, to remain below the range of flammability the propane spurt has to be mixed with about 4 l of air.

Human Skin Exposure.

Evaluation of possible damage to human skin during spray was examined by spraying human forearms for spurt duration up to 200ms with the 1.6 mm bore nozzle at 30 mm distance. No damage was observed either immediately or after several days of follow up. The maximum force onto the skin for the 1.6 mm nozzle 38 covering a 10 mm diameter spot is up to 2.6% of the pressure in the container, i.e., applying pressure at the target site up to about 0.15 MPa (1.4 atm). The cryogen impact on the skin was monitored with a high speed video camera (Fast Cam PCI R2, Photron, San Diego Calif.). This momentum flux depressed the skin surface by several millimeters, but the skin returned to original position less than 10 ms after the spurt. This bouncing back of the skin also removed all debris of ice from the surface. This is in contrast to spurts of liquid cryogen where a liquid deposit and ice formed from the ambient air frequently remain for several tens of milliseconds after the spurt.

A compression of the dermis could, in principle, force blood out of the vessels. This phenomenon might be an advantage in treating deeper located targets such as the bulb of the hair follicles since the optical absorption the upper layers is reduced. However, it might be a disadvantage in treating shallowly located blood vessels such as in the case of port wine stains. This effect was studied by evaluating the purpura introduced by laser exposure typically used during treatment of port wine stains. The laser (Sclero-Plus, Candela Corp. Inc. Wayland Mass.) was set either to 7 J/cm$^2$ or to 8 J/cm$^2$, pulse duration 1.5 ms and wavelength 585 nm. The results from exposure to normal skin of Caucasian forearms (palmar side) are summarized in Table 5. The diameter of the irradiated spot was 7 mm, and the cooling of the spot was aligned with carbon dioxide spray 40 from a 1.6 mm bore nozzle 38 at 30 mm distance from the skin. See nozzle performance in the graph of FIG. 6. The results were evaluated at 22 h and 50 h after exposure. Purpura was evaluated visually on a scale from 1 to 10 where 10 was set to the value for the noncooled control.

TABLE 5

| Delay | 10 ms | 30 ms | 50 ms |
|---|---|---|---|
| Spurt duration 25 ms | 8 (9) | 7 (4) | 6 (3) |
| Spurt duration 50 ms | 7 (4) | 6 (3) | 6 (3) |
| Spurt duration 75 ms | 8 (9) | 6 (4) | 0 (0) |
| Spurt duration 100 ms | 8 (9) | 4 (3) | 0 (0) |

All exposed spots exhibited a well-demarked edema 2 h after exposure. Purpura developed during 12 h after exposure. However, the results indicate that purpura only was minor affected for the shortest cooling duration and delay, i.e., from a maximum score of 10 for the non-cooled control site to 7-10. This seems to indicate that the blood remains in the vessels during the cooling spray. The smaller score values are observed for the spots irradiated 125-150 ms after onset of the spurt. This time correspond to the delay for a thermal wave to propagate through an epidermal layer of about 100 μm. Thus, the results indicate that the time dynamic is too fast to force blood out of the capillaries in papillary/reticular dermis, and that the reduction of purpura for long delays is due to protection of these vessels by the cooling.

In summary, with respect to the global warming potential propane (GWP=3) seems to be an excellent replacement for tetrafluoroethane (GWP=1300). However, the high flammability of propane is believed to be unsatisfactory for medical laser treatments when used without a shielding gas. A commercial brand of liquid propane adheres very well to the surface, resulting in a high heat transfer coefficient. This very high transfer coefficient might indicate that the cooling efficiency might be acceptable even when reduced by the presence of a shielding gas.

A premix of propane/butane with a non-flammable compound before spraying rather than using a shielding gas has several advantages. A pressurized mixture of, e.g., 50% liquid propane and 50% liquid carbon dioxide at room temperature have a pressure of 3.7 MPa, i.e., 35% lower than for 100% $CO_2$, and a mixture of propane at less than 9.4% in carbon dioxide is by federal regulation classified as a non-flammable mixture. Secondly, the requirements for an efficient adiabatic expansion of carbon dioxide for forming dry ice after leaving the nozzle are reduced. A slurry consisting of a mixture of dry ice crystal and liquid propane has a very good wetting of the skin surface, resulting in a high heat transfer coefficient. Thus, the momentum flux transferred to the skin surface is reduced. These properties are expected to be preferred for treating lesions as port wine stains in regions with thin skin such as in the ocular orbit.

Liquid carbon dioxide (GWP=1) can also be used as the only cryogen. However, the momentum flux of the spray is high, and the skin surface is somewhat depressed. This is an advantage in treating deeper located target such as the bulb of the hair follicle, but it might represent a problem for shallowly located targets such as the ectatic capillaries of port wine stain. However, preliminary measurements on normal skin indicate that the blood remain in the capillaries for spurt durations in the range of 50-100 ms. All residual dry ice or ice from ambient air humidity bounced off the skin surface as it relaxed back about 10 ms after the spray, leaving a clean skin surface. No skin damage was observed due to the cryogen spurts up to 200 ms duration. Finally it should be noted that although carbon dioxide by definition has a global warming potential equal to one, the real value GWP is zero for $CO_2$ made from sources other than burning of fossil fuels. Industrial $CO_2$ production is, e.g., made from fermentation of corn in alcohol production. Thus, the use contemplated by the invention represents a recycling of $CO_2$ made from solar irradiation.

In summary, the illustrated embodiments of the invention include, but are not limited to an improvement in a method for providing localized cooling of tissue when thermally mediated by electromagnetic radiation comprising the steps of applying a predetermined amount of a flammable heat transferring substance onto a selected location on the tissue; and preventing ignition of the heat transferring substance by heating from the electromagnetic radiation.

The step of applying a predetermined amount of the heat transferring substance onto the selected location on the tissue comprises the step of directing a predetermined amount of potentially flammable coolant onto the selected location and where preventing ignition of the heat transferring substance by heating from the electromagnetic radiation comprises shielding the heat transferring substance from oxygen in an ambient environment.

The step of preventing ignition of the heat transferring substance by heating from the electromagnetic radiation comprises mixing a potentially flammable coolant with an inert substance to provide a substantially nonflammable mixture prior to directing applying the heat transferring substance mixed with the inert substance onto a selected location on the tissue.

The step of preventing ignition of the heat transferring substance by heating from the electromagnetic radiation comprises employing an inert heat transfer substance as the heat transferring substance.

The step of employing an inert heat transfer substance comprises employing liquid carbon dioxide under pressure as the heat transferring substance, and adiabatically expanding the liquid carbon dioxide to provide a solid carbon dioxide spray onto the selected location.

The step of preventing ignition of the heat transferring substance by heating from the electromagnetic radiation comprises employing a substantially nonflammable liquid propane or butane mixed with liquid carbon dioxide under pressure as the heat transferring substance, and adiabatically expanding the liquid propane or butane mixture with the liquid carbon dioxide to provide a mixture of liquid propane or butane with solid carbon dioxide onto the selected location.

The illustrated embodiments also include a method for performing laser treatment of a biological tissue comprising the steps of cooling a selected portion of the biological tissue using a spray of a predetermined amount of potentially flammable cryogenic fluid; radiating the selected portion of the biological tissue with energy to produce heat in the biological tissue while leaving a superficial part of the biological tissue substantially undamaged, the superficial part of the biological tissue being cooled by the cryogenic fluid, the heat being dissipated by the cryogenic liquid applied to the superficial part of the biological tissue, the amount of dissipation of the heat from the superficial part of the biological tissue being controlled by the predetermined amount of the cryogenic fluid applied to the superficial part of the biological tissue; and rendering the potentially flammable cryogenic fluid nonignitable by the radiation applied the selected portion of the biological tissue.

The step of rendering the potentially flammable cryogenic fluid nonignitable by the radiation applied the selected portion of the biological tissue comprises providing a shielding gas with the potentially flammable cryogenic fluid.

The step of providing the shielding gas with the potentially flammable cryogenic fluid comprises providing a concentric flow of argon, nitrogen or carbon dioxide surrounding the potentially flammable cryogenic fluid.

The step of cooling the selected portion of the biological tissue using a spray of a predetermined amount of potentially flammable cryogenic fluid comprises cooling the selected portion of the biological tissue using a spray of dimethyl ester, propane, isobutene or mixtures thereof.

The step of rendering the potentially flammable cryogenic fluid nonignitable by the radiation applied the selected portion of the biological tissue comprises mixing a flammable liquid cryogen and a shielding gas to form a mixture before cooling the selected portion of the biological tissue with the mixture.

The step of mixing a liquid flammable cryogen and a shielding gas comprises mixing carbon dioxide with the liquid cryogen in a common pressurized container and where cooling a selected portion of the biological tissue using a spray comprises spraying the mixture onto the selected portion of the biological tissue through a common valve and nozzle.

The illustrated embodiments also include a method for performing laser treatment of a biological tissue comprising the steps of cooling a selected portion of the biological tissue using a spray of a predetermined amount of liquid carbon dioxide through at least one nozzle which is arranged and configured to adiabatically expand the liquid carbon dioxide rendering it as carbon dioxide snow sprayed onto the selected portion of the biological tissue; and radiating the selected portion of the biological tissue with energy to produce heat in the biological tissue while leaving a superficial part of the biological tissue substantially undamaged, the superficial part of the biological tissue being cooled by the carbon dioxide snow, the heat being dissipated by the carbon dioxide snow applied to the superficial part of the biological tissue, the amount of dissipation of the heat from the superficial part of the biological tissue being controlled by the predetermined amount of the carbon dioxide snow applied to the superficial part of the biological tissue.

The method further comprises the step of mixing the liquid carbon dioxide with liquid propane in an amount effective to render the mixture nonflammable and where cooling the selected portion of the biological tissue using a spray is arranged and configured so that the spray delivers a slurry of liquid propane droplets with carbon dioxide snow onto the selected portion of the biological tissue.

The illustrated embodiments also include a method for performing laser treatment of a biological tissue comprising the steps of mixing liquid propane with air into a spray in an amount sufficient to render the liquid propane and air mixture nonflammable; cooling a selected portion of the biological tissue using the spray of a predetermined amount of liquid propane and air mixture; radiating the selected portion of the biological tissue with energy to produce heat in the biological tissue while leaving a superficial part of the biological tissue substantially undamaged, the superficial part of the biological tissue being cooled by the sprayed liquid propane and air mixture, the heat being dissipated by the liquid propane and air mixture applied to the superficial part of the biological tissue, the amount of dissipation of the heat from the superficial part of the biological tissue being controlled by the predetermined amount of the liquid propane and air mixture applied to the superficial part of the biological tissue.

Still further, the illustrated embodiments of the invention include an apparatus for thermally mediating tissue using electromagnetic radiation comprising a source of a flammable heat transferring substance; a source of electromagnetic radiation; a sprayer which applies a predetermined amount of the flammable heat transferring substance onto a selected location on the tissue; and means combined with the sprayer for preventing ignition of the heat transferring substance from heating by the source of electromagnetic radiation.

The means for preventing ignition of the heat transferring substance comprises a source of a nonflammable substance communicated to the sprayer and where the sprayer is arranged and configured to provide for a region of the nonflammable substance surrounding the heat transferring substance to shield the heat transferring substance from oxygen in an ambient environment.

The means for preventing ignition comprises a source of a nonflammable substance communicated to the sprayer and where the sprayer provides a substantially nonflammable mixture of the heat transferring substance and the nonflammable substance onto a selected location on the tissue.

The source of a nonflammable substance is a source of liquid carbon dioxide under pressure and where the sprayer mixes the heat transferring substance, and allows the liquid carbon dioxide to adiabatically expand to create a solid carbon dioxide slurry to be sprayed with the heat transferring substance onto the selected location.

The illustrated embodiments of the invention include an apparatus for performing laser treatment of a biological tissue comprising a laser directed to deliver energy to a selected location of the biological tissue; a source of liquid carbon dioxide; a controller; and a spray applicator having at least one nozzle communicated with the source of liquid carbon dioxide, coupled to and controlled by the controller to spray a predetermined amount of liquid carbon dioxide through the at least one nozzle to adiabatically expand the liquid carbon dioxide to create a controlled amount of carbon dioxide snow which impinges onto the selected location of the biological tissue.

The apparatus further comprises a source of liquid propane communicated to the spray applicator, the spray applicator mixing the liquid carbon dioxide with liquid propane as controlled by the controller in an amount effective to render the mixture nonflammable and to deliver a slurry of liquid propane droplets with carbon dioxide snow onto the selected portion of the biological tissue.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An improvement in a method comprising providing localized cooling of external tissue when thermally mediated by electromagnetic radiation;
   radiating a selected surface portion of the external tissue with electromagnetic energy to produce heat in the external tissue while leaving a superficial part of the external tissue substantially undamaged, the improvement comprising:
   applying a predetermined amount of liquid propane onto the selected location on the surface portion of the external tissue by means of a sprayer; and
   providing source of liquid carbon dioxide that has been premixed with the liquid propane under pressure in a common container so that when applying the predetermined amount of liquid propane to the external tissue, the liquid propane is rendered noncombustible and further cools the external tissue, wherein the liquid carbon dioxide under pressure is adiabatically expanded during application to the external tissue to provide a solid carbon dioxide and liquid propane spray directly onto the selected location on the surface of the external tissue.

2. The improvement of claim 1 where applying a predetermined amount of the first heat transferring substance onto the selected location on the surface of the external tissue by means of a sprayer comprises directing a predetermined amount of coolant directly onto the selected location.

3. A method for performing laser treatment of a biological tissue comprising:
   applying a pressure impulse on a predetermined target site on the biological tissue arising from the momentum flux of sprayed carbon dioxide incident on the biological tissue sufficient to depress the skin by more than one millimeter at the target site;
   cooling the predetermined target site on the biological tissue by spraying a predetermined amount of premixed liquid carbon dioxide and liquid propane under pressure in a common container through at least one nozzle, the nozzle adiabatically expanding the liquid carbon dioxide to produce a carbon dioxide snow which renders the liquid propane noncombustible; and
   radiating the selected portion of the biological tissue with energy to produce heat in the biological tissue while leaving a superficial part of the biological tissue substantially undamaged, the superficial part of the biological tissue being cooled by a slurry of carbon dioxide snow and liquid propane resulting from the sprayed pre-mixture of liquid carbon dioxide and liquid propane, the heat being dissipated by the carbon dioxide snow and liquid propane slurry applied to the superficial part of the biological tissue, the amount of dissipation of the heat from the superficial part of the biological tissue being controlled by the predetermined amount of the carbon dioxide snow and liquid propane applied to the superficial part of the biological tissue,
   whereby inherent mediation of any pain sensation arising from the radiation is at least partially masked by the pressure impulse and/or by the temperature of the carbon dioxide snow and liquid propane.

4. The method of claim 3 where applying the pressure impulse on a predetermined target site on the biological tissue comprises applying up to 0.15 MPa of pressure at the target site.

5. A method for performing laser treatment of a biological tissue comprising:
   cooling a selected portion of the biological tissue using a spray of a predetermined amount of premixed liquid carbon dioxide and liquid propane through at least one nozzle which is arranged and configured to adiabatically expand the liquid carbon dioxide rendering it as carbon dioxide snow sprayed onto the selected portion of the biological tissue, wherein the carbon dioxide snow is substantially all deposited on the biological tissue in a solid state and which renders the liquid propane; and
   radiating the selected portion of the biological tissue with energy to produce heat in the biological tissue while leaving a superficial part of the biological tissue substantially undamaged, the superficial part of the biological tissue being cooled by the carbon dioxide snow and liquid propane, the heat being dissipated by the carbon dioxide snow and liquid propane applied to the superficial part of the biological tissue, the amount of dissipation of the heat from the superficial part of the biological tissue being controlled by the predetermined amount of the carbon dioxide snow and liquid propane applied to the superficial part of the biological tissue,
   whereby deposition of the carbon dioxide snow on the biological tissue substantially all in the solid state avoids pooling of any substantial amount of liquid state propane and consequent uneven cooling of the biological tissue.

\* \* \* \* \*